(12) United States Patent
Cervantes et al.

(10) Patent No.: US 7,753,876 B2
(45) Date of Patent: Jul. 13, 2010

(54) EXPANDABLE JAW DRUG DELIVERY CATHETER

(75) Inventors: Marvin J. Cervantes, Santa Rosa, CA (US); Kevin Knoll, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1115 days.

(21) Appl. No.: 10/842,664

(22) Filed: May 10, 2004

(65) Prior Publication Data

US 2005/0251106 A1 Nov. 10, 2005

(51) Int. Cl.
*A61M 29/00* (2006.01)
(52) U.S. Cl. ...................................... 604/106
(58) Field of Classification Search ................ 604/523, 604/104, 103.01, 103.02, 103.05, 103.08, 604/105, 106, 107, 108, 96.01
See application file for complete search history.

(56) References Cited

U.S. PATENT DOCUMENTS

| | | | |
|---|---|---|---|
| 5,087,244 A | 2/1992 | Wolinsky et al. | |
| 5,112,305 A | 5/1992 | Barath et al. | |
| 5,279,565 A | 1/1994 | Klein et al. | |
| 5,415,637 A * | 5/1995 | Khosravi | 604/105 |
| 5,713,863 A * | 2/1998 | Vigil et al. | 604/104 |
| 6,102,887 A * | 8/2000 | Altman | 604/22 |
| 6,280,413 B1 * | 8/2001 | Clark et al. | 604/104 |
| 6,280,414 B1 * | 8/2001 | Shah et al. | 604/104 |
| 6,409,716 B1 | 6/2002 | Sahatjian et al. | |
| 6,544,223 B1 | 4/2003 | Kokish | |

* cited by examiner

*Primary Examiner*—Nicholas D Lucchesi
*Assistant Examiner*—Christopher D Koharski (57) ABSTRACT

A system for treating a vascular condition includes a catheter having a drug delivery lumen and an expandable jaw device at the distal end of the catheter. The jaw device includes drug delivery ports in communication with the lumen, so that a therapeutic agent can be delivered to a treatment site. Another embodiment provides a method for expanding a jaw device at a treatment site and delivering a therapeutic agent. Another embodiment includes a catheter having an expandable member with hollow needles disposed on the outer surface of the expandable member. Yet another embodiment provides a method for expanding the expandable member at a treatment site and delivering a therapeutic agent into the tissue.

10 Claims, 5 Drawing Sheets

EXPANDABLE JAW DRUG DELIVERY CATHETER

FIELD OF THE INVENTION

This invention relates generally to the delivery of therapeutic agents to a target site within the vasculature of a patient. More specifically, the invention relates to a catheter with an expandable member at the distal tip of the catheter that is capable of delivering a therapeutic agent to the vascular tissue.

BACKGROUND OF THE INVENTION

Cardiovascular disease, including atherosclerosis, is a leading cause of death in the U.S. A number of methods and devices for treating coronary heart disease have been developed, some of which are specifically designed to treat the complications resulting from atherosclerosis and other forms of coronary arterial narrowing.

One method of treating atherosclerosis and other forms of coronary narrowing is percutaneous transluminal coronary angioplasty, hereinafter referred to as "angioplasty" or "PTCA". Many heart disease patients undergo angioplasty, some repeatedly.

The objective of angioplasty is to enlarge the lumen of the affected coronary artery by radial hydraulic expansion. This is generally accomplished by inflating a balloon within the narrowed lumen of the affected artery. Radial expansion of the coronary artery may occur in several different dimensions, and is related to the nature of the plaque. Soft, fatty plaque deposits are flattened by the balloon, while hardened deposits are cracked and split to enlarge the lumen. The wall of the artery itself may also be stretched as the balloon is inflated.

With simple angioplasty, the balloon is threaded through the artery with a catheter and inflated at the place where the blood vessel is blocked. After the procedure, the balloon is removed. Following simple angioplasty alone, arteries frequently close up again or re-narrow. This re-narrowing is known as restenosis.

To reduce the risk of restenosis, a stent may be inserted during angioplasty. The stent may be used to support plaque damaged arterial walls and maintain the internal lumen of the artery after a blockage has been removed. The use of a stent may significantly reduce the risk of restenosis, but it does not eliminate it.

Blood vessel wall injury when the stent is implanted is, in fact, one cause of restenosis. The area around the stent becomes inflamed and new cells form scar tissue. The arterial walls may become so thick that, in some instances, they protrude into the mesh of the stent. In such cases, another angioplasty procedure may be performed, and a new stent may be placed inside the existing one.

One means of reducing the incidence of restenosis is delivering a drug at the angioplasty site. Drug coated stents have been used for this purpose. The stent may be coated, for example, with rapamycin analogs or rapamycin derivatives. This drug is used to prevent organ rejection in kidney transplants. It stops new cells from forming without impairing the healing of the vessel. It also dampens inflammation and has antibiotic properties. In clinical studies, patients who received stents coated with rapamycin analogs or rapamycin derivatives exhibited a substantially reduced re-narrowing and re-blockage of treated arteries.

Another means of reducing restenosis is by delivering a therapeutic agent directly to the treatment site during the angioplasty procedure. For example, U.S. Pat. No. 5,087,244 describes a catheter with an expandable balloon near its distal tip. The balloon is filled with the therapeutic agent to be delivered, and expands until it contacts the vessel wall. The therapeutic agent flows out of the balloon through holes in the balloon surface and bathes the vessel wall.

U.S. Pat. No. 6,544,223 describes an inflatable balloon having a plurality of holes through the surface of the balloon. A microporous coating covers at least a portion of the outer surface of the balloon. The thickness of the coating and the size of the micropores permit controlled delivery of a therapeutic substance to the vessel wall.

U.S. Pat. No. 5,112,305 describes a catheter with an expandable balloon. Disposed about the outer surface of the balloon are a plurality of tubular extensions. The balloon is placed at a treatment site, and a therapeutic agent is used to expand the balloon abruptly, causing the tubular extensions to puncture the vessel wall, and deliver the therapeutic agent into the vessel wall.

U.S. Pat. No. 6,409,716 discloses a catheter with an expandable member near the distal end of the catheter. At least a portion of the expandable member is coated with a swellable hydrogel polymer. Incorporated in the hydrogel polymer is an aqueous solution of a drug that is to be delivered to the tissue. The drug is released during compression of the hydrogel polymer coating against the wall of the vessel when the expandable member is expanded.

Although all of these systems provide a means for delivering a therapeutic agent to a localized site on a vessel wall, they require an expandable balloon, which occludes blood flow through the vessel during delivery of the therapeutic agent and prevents perfusion of tissue downstream from the treatment site. Consequently, such devices can usually be deployed for only a few minutes, limiting the amount of the therapeutic agent that can be delivered.

U.S. Pat. No. 5,279,565 discloses a catheter with a movable support frame near the distal end of the catheter. The support frame is operated by an actuator shaft and moves between a retracted position adjacent to the catheter body and a deployed position radially extended from the catheter body. On the external surface of the support frame is a rigid platform having a radially-facing contact surface with a delivery interface for delivering the therapeutic agent. The delivery interface may be a porous rigid matrix, a manifold of tubes with radially-facing perforations, a bladder having a plurality of perforations on its radially-facing surface or a detachable porous membrane for applying a cell graft to the treatment site. Although this device allows blood to flow freely while it is deployed, it applies the therapeutic agent only to the surface of the treatment site.

It would be desirable therefore, to provide a device and method of delivering a therapeutic agent to a treatment site within the vascular system that would overcome these and other limitations while delivering the therapeutic agent to a defined depth within the vascular tissue.

SUMMARY OF THE INVENTION

One embodiment of the invention provides a system for treating a vascular condition comprising a catheter having a drug delivery lumen and at least one expandable jaw device operably attached to the distal end of the catheter. The jaw device includes a plurality of drug delivery ports in communication with the drug delivery lumen, so that a therapeutic agent is deliverable to the drug delivery ports of the jaw by way of the drug delivery lumen of the catheter.

Another embodiment of the invention provides a method for treating a vascular condition, the method comprising delivering at least one jaw device adjacent to a target region of a vessel via a catheter, expanding the jaw device against the target region of the of the vessel, and delivering a therapeutic agent via the catheter and through the drug delivery ports in the jaw device to the target region of the vessel.

Another embodiment of the invention provides a system for treating a vascular condition comprising a catheter having a drug delivery lumen and an expandable member at the distal end of the catheter. The expandable member includes a plurality of hollow slat portions. Extending radially outward from the slat portions are a plurality of delivery needles that are connected to the drug delivery lumen through the hollow slat portions. A therapeutic agent can be delivered via the drug delivery lumen of the catheter, through the delivery needles, and to a target site.

Another embodiment of the invention provides a method for treating a vascular condition, the method comprising delivering an expandable member with hollow needles disposed on the outer surface of the expandable member to a target region of a vessel via a catheter. At the target site, the expandable member is expanded so that the hollow needles penetrate the vascular tissue to a defined depth and deliver a therapeutic agent into the vascular tissue.

The present invention is illustrated by the accompanying drawings of various embodiments and the detailed description given below. The drawings should not be taken to limit the invention to the specific embodiments, but are for explanation and clarity. The detailed description and drawings are merely illustrative of the invention rather than limiting, the scope of the invention being defined by the appended claims and equivalents thereof. The forgoing aspects and other attendant advantages of the present invention will become more readily appreciated by the detailed description taken in conjunction with the accompanying drawings.

DETAILED DESCRIPTION

Figures 1A, 1B, 1C, 1D:
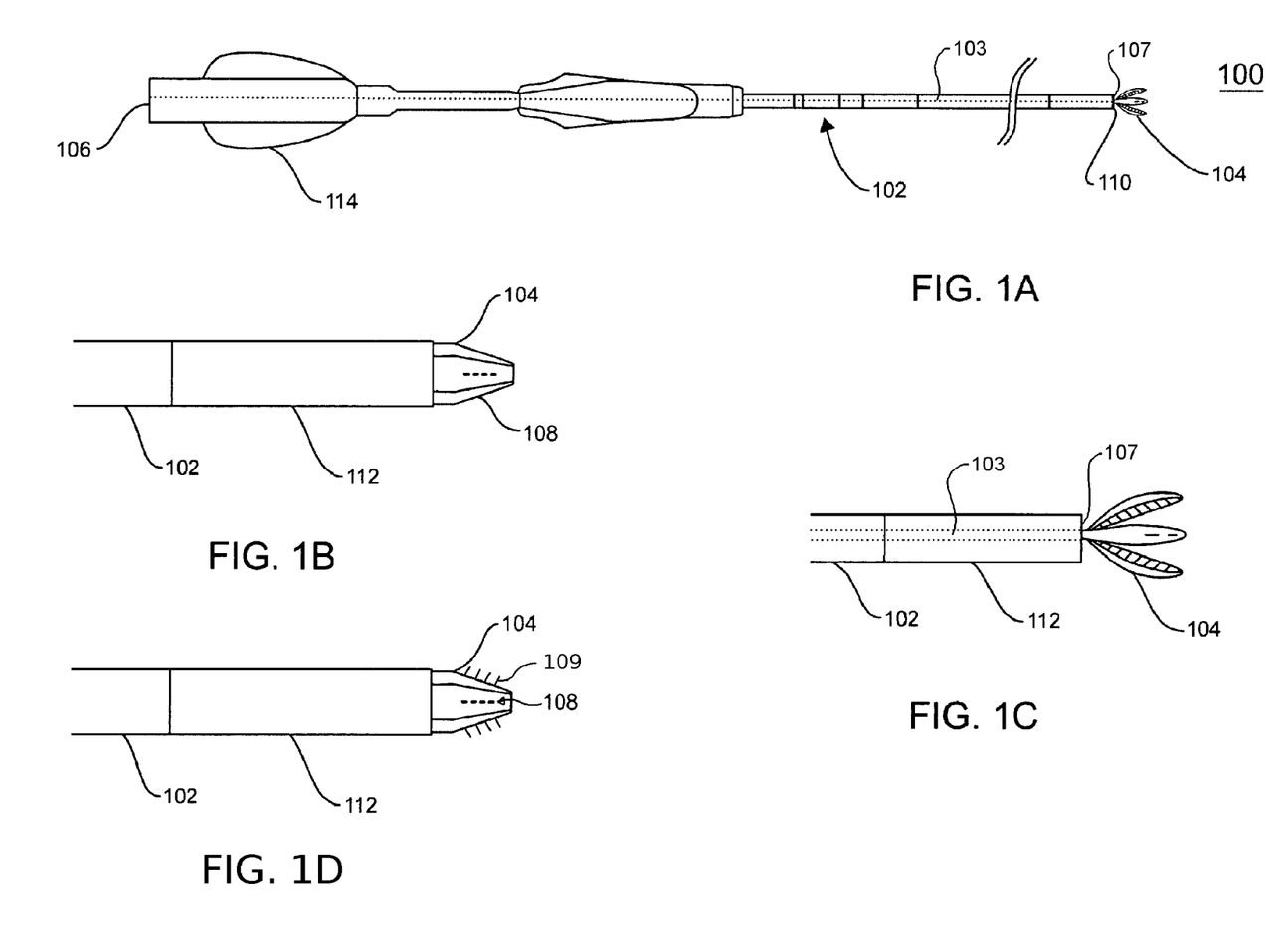
FIG. 1A is a schematic view of one embodiment of a system for treating a vascular condition comprising a catheter having jaw member at the distal tip of the catheter, in accordance with the present invention.
FIG. 1B is a schematic representation of the distal portion of the delivery system shown in FIG. 1A with the jaw member in a closed configuration, in accordance with the present invention.
FIG. 1C is a schematic representation of the distal portion of the delivery system shown in FIG. 1A with the jaw member in an expanded configuration, in accordance with the present invention.
FIG. 1D is a schematic representation of the distal portion of another embodiment of a delivery system with the jaw member in a closed configuration, in accordance with the present invention.

Referring to the drawings, FIG. 1A is a schematic representation of a system 100 for treating a vascular condition. System 100 comprises a catheter 102, having an expandable jaw device 104 at the distal tip of the catheter 102. Jaw device 104 a plurality of delivery ports 108 (shown in FIG. 1B) configured to contact the inner wall of the blood vessel at a treatment site, and deliver a therapeutic agent to the site.

The catheter body 102 is typically made of a flexible, biocompatible polymeric material such as polyurethane, polyethylene, nylon, or polytetrafluroethylene (PTFE). In one embodiment, the catheter 102 has a lumen (not shown) that can accommodate a guide wire. The lumen runs longitudinally through the catheter 102, so that the catheter may be slipped over the guide wire, and, when no longer needed, the guide wire may be withdrawn through the lumen of the catheter. A guide wire is typically of metallic construction, and is inserted through the femoral artery and threaded through the vascular system to the target site. The catheter is slipped over the guide wire, and guided along the vascular route, until both the guide wire and catheter are at their desired target locations.

In one embodiment of the invention, the catheter 102 has a drug delivery lumen 103, illustrated by the dashed line. This lumen runs longitudinally through the catheter 102 from the proximal end 106, and is in fluidic communication with the expandable jaw device 104 at the distal tip 107 of the catheter 102. The jaw segments of the jaw device 104 are hollow, so that a therapeutic agent can pass from the drug delivery lumen, through the jaw segments to the drug delivery ports on the external surface of the jaw device. At the proximal end 106 of the catheter 102 is a fitting that can accommodate a syringe. This fitting may be, for example, a pressure fitting or a luer fitting. The syringe fitting is configured so that the syringe will fluidically communicate with the drug delivery lumen when the syringe is installed on the fitting.

Expandable jaw device 104 is attached adjacent the distal tip of the catheter 102 and comprises a plurality of jaw segments. At the proximal end of expandable jaw device 104 is a hinge 110 so that the distal ends of the jaw segments can diverge from each other to form an open configuration. In one embodiment of the invention, the jaw device 104 is self-expanding, and comprises a self-expanding material such as nitinol. In another embodiment of the invention, a spring at the proximal end of the jaw device causes the jaw device to assume an open configuration.

FIG. 1B is a schematic representation of the distal portion of delivery catheter 102 in which the jaw device 104 is in a closed configuration. In one embodiment of the invention, the jaw segments are hollow and have a plurality of delivery ports 108 disposed on the external surface of the jaw segments. In one embodiment of the invention, the delivery ports 108 are hollow needles 109, as shown in FIG. 1D. The outer surface of the jaw segments is configured so that when the jaw device 104 is in an open configuration, as shown in FIG. 1C, the hollow needles will penetrate the vessel wall to a defined depth. In one embodiment of the invention, the jaw segments are of a sufficient number and size so that in the expanded configuration, the jaw device contacts a substantial portion of the target region of the vessel wall.

In one embodiment of the invention, the distal portion of catheter body 102 is surrounded by a retractable sheath 112, as shown in FIG. 1B. Sheath 112 at least partially covers at least the proximal portion of jaw device 104, and maintains the jaw device 104 in a closed configuration. The sheath 112 is connected to a lever 114, shown in FIG. 1A, at the proximal end of catheter 102 that allows the operator to retract the sheath 112. When the sheath 112 is retracted, the jaw device 104 opens, as shown in FIG. 1C.

In another embodiment of the invention, the jaw device 104 is mounted on an inner catheter that is connected to lever 114, and can be moved longitudinally by a connecting rod or wire that passes through catheter body 102. By advancing the rod in a distal direction, the jaw device 104 is moved distally, and assumes an open configuration.

In one embodiment of the invention, the device 100 can be used to deliver a drug or therapeutic agent into the vascular system. A therapeutic agent is capable of producing a beneficial effect against one or more conditions including coronary restenosis, cardiovascular restenosis, angiographic restenosis, arteriosclerosis, hyperplasia, and other diseases and conditions. The therapeutic agent may comprise, for example an antirestenotic drug, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, an organic drug, a pharmaceutical compound, a recombinant DNA product, a recombinant RNA product, a collagen a collagenic derivative, a protein, a protein analog, a saccharide, a saccharide derivative, a bioactive agent, a pharmaceutical drug, a therapeutic substance, or combinations thereof.

After a therapeutic agent has been delivered to the treatment site, jaw device 104 is returned to a closed configuration, as shown in FIG. 1B, and the catheter 102 is removed from the patient. In order to close the jaw device 104, in one embodiment of the invention, the sheath 112 is returned to a distal position in which at least a proximal portion of the jaw device 104 is surrounded by the sheath. In another embodiment of the invention, the jaw device is drawn into the interior lumen of the catheter by using the lever 114 to retract the connecting rod. In either case, the proximal portion of the external surface of jaw device 104 is tapered so that as either the sheath 112 or the distal end of the catheter body 102 will engage the surface of the jaw segments, and slide over them causing them to close.

Figure 2:
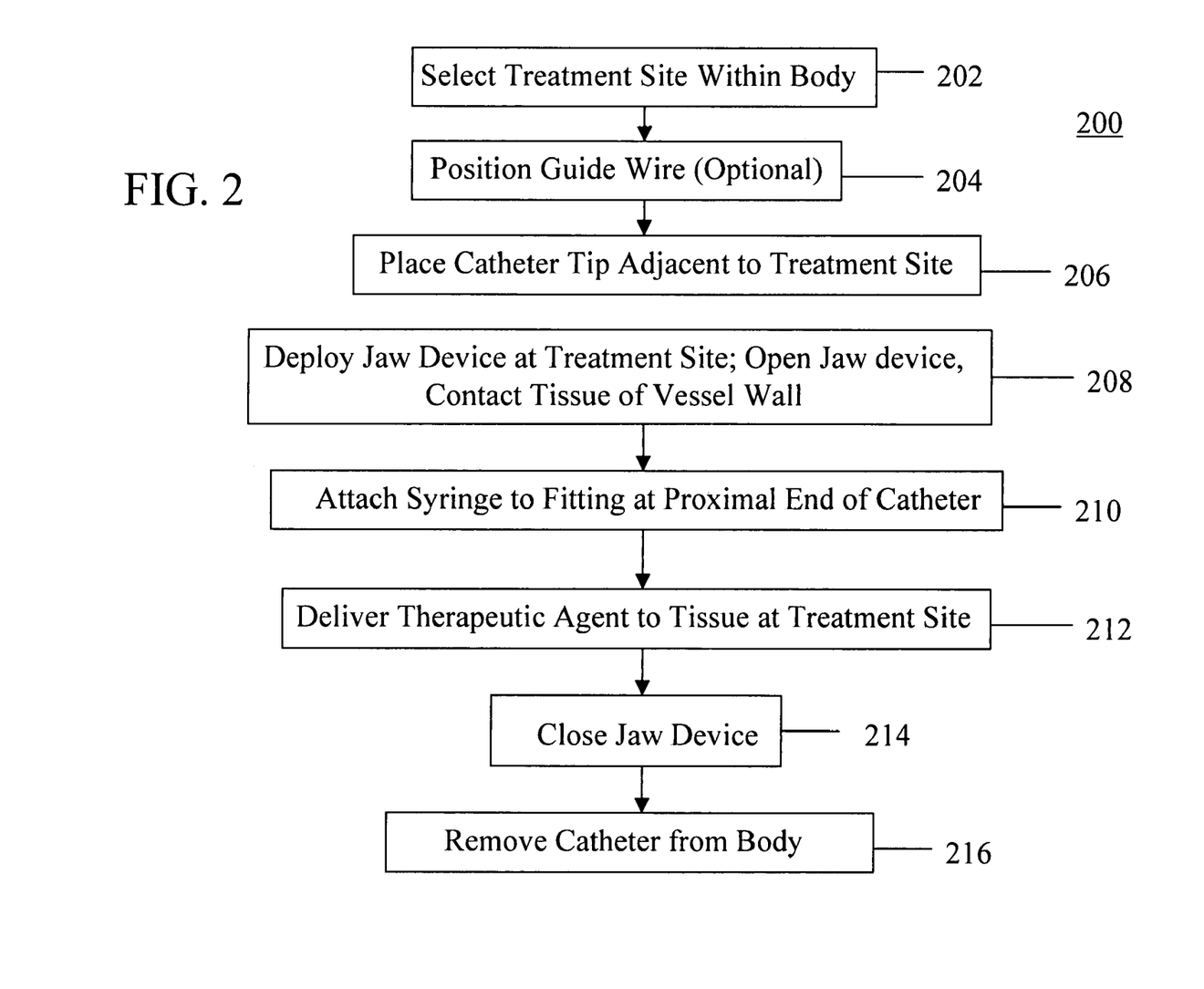
FIG. 2 is a flow diagram of a method for delivering a therapeutic agent to a target site, in accordance with the present invention.

Another embodiment of the invention includes a method 200 for treating a vascular condition, as illustrated in a flow diagram in FIG. 2. The method 200 begins at block 202 wherein a treatment, or target, site is selected. Next, as indicated in block 204, a guide wire may be inserted into the femoral artery or at another site, advanced to the target site, and positioned so that the distal tip of the guide wire is adjacent to the target site. The catheter may be slipped over the guide wire and threaded through the vascular system. Whether or not a guide wire is used, the distal tip of the catheter is placed adjacent to the target site, as indicated in block 206. As indicated in block 208, the jaw device is deployed at the treatment site. Deployment of the jaw device is accomplished either by retracting the sheath or by advancing the jaw device out of an inner lumen of the catheter. The jaw device is opened until the outer surface of the jaw device contacts the vessel wall, and the needles, if present, pierce the tissue of the vessel wall.

A syringe containing the therapeutic agent to be delivered to the treatment site is attached to a fitting at the proximal end of the catheter, as indicated in block 210. The therapeutic agent is then injected from the syringe, through the delivery lumen of the catheter, through the jaw segments and out through the drug delivery ports, as indicated in block 212. If the drug delivery ports include needles, the therapeutic agent is injected through the needles into the tissue of the vessel wall at a defined depth determined by the length of the needles.

As indicated in block 214, the jaw device is returned to a closed configuration. This may accomplished either by advancing the retractable sheath over the jaw segments, or by retracting the jaw device into the lumen of the catheter. Finally, as indicated in block 216, the catheter may be removed from the body.

Figure 3A:
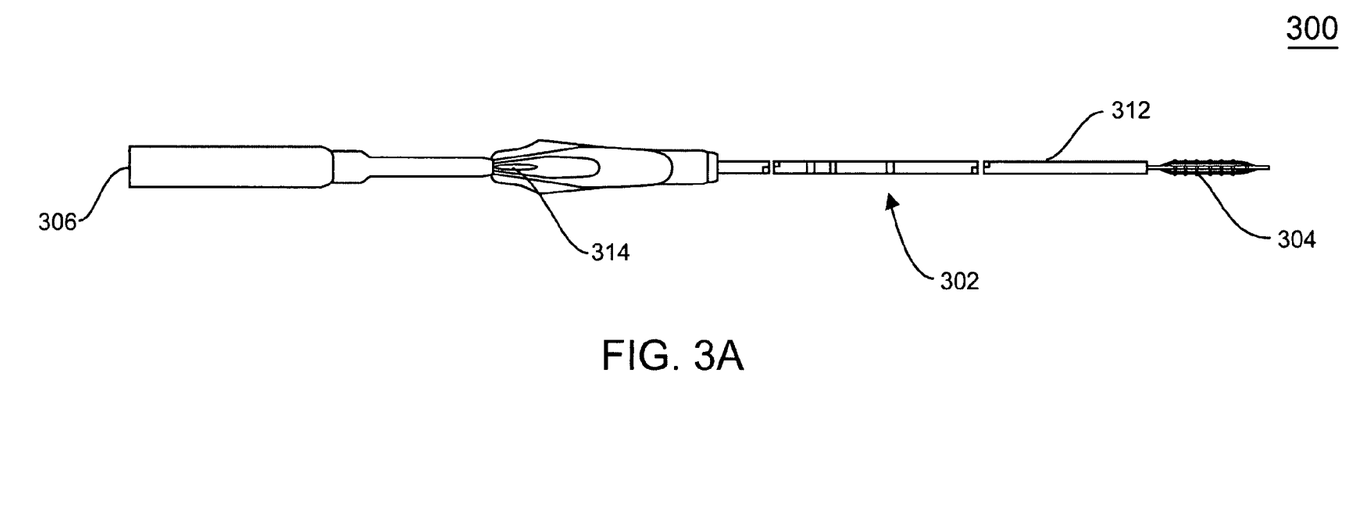
FIG. 3A is a schematic view of another embodiment of a system for treating a vascular condition comprising a catheter having an expandable member at the distal tip of the catheter, in accordance with the present invention.

Yet another embodiment of the invention is represented schematically in FIG. 3A. System 300 comprises a catheter 302 having an expandable member 304 at the distal tip of the catheter 302. Expandable member 304 provides means for contacting the inner wall of the blood vessel at the treatment site, and delivering a therapeutic agent to the site. Catheter 302 includes an internal drug delivery lumen (not shown), and a fitting 306 configured to accommodate a syringe at the proximal end of the catheter 302.

Figure 3B:
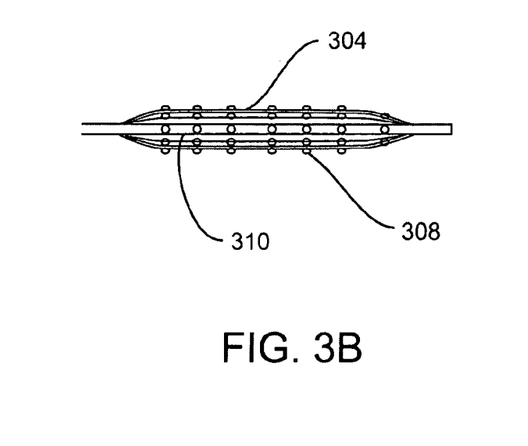
FIG. 3B is a schematic representation of the distal portion of the delivery device shown in FIG. 3A with the expandable member in a contracted configuration in accordance with the present invention.

In one embodiment of the invention, the distal portion of catheter body 302 is surrounded by a retractable sheath 312. The sheath 312 is connected to a lever 314 that enables the operator to retract or engage the sheath 312. When engaged, the sheath 312 covers at least the proximal portion of the expandable member 304, and maintains the expandable member 304 in a closed configuration as shown in FIG. 3B. In another embodiment of the invention, the expandable member 304 is mounted on an inner catheter that is connected to lever 314, and can be moved longitudinally by a connecting rod or wire that passes through a lumen of catheter body 302. Expandable member 304 is positioned within the distal portion of the lumen of the catheter 302. Advancing the rod in a distal direction moves the expandable member 304 distally, until the expandable member 304 is positioned adjacent to the distal tip of the catheter 302, as shown in FIG. 3A.

Figure 3C:
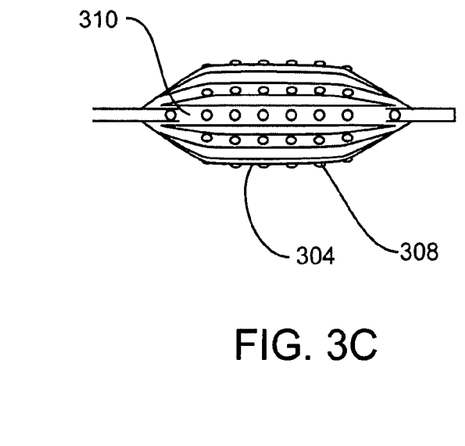
FIG. 3C is a schematic representation of the distal portion of the delivery device shown in FIG. 3A with the expandable member in an expanded configuration, in accordance with the present invention.

In one embodiment of the invention, expandable member 304 comprises hollow tubular slats 310, as shown in FIGS. 3B and 3C. The hollow slats 310 include a lumen in fluidic communication with the drug delivery lumen of catheter 302. Slats 310 comprise a suitable material, such as metals, titanium, metal alloys, stainless steel, polypropylene, polyethylene, medically approved polymers, and combinations thereof. A plurality of hollow drug delivery needles 308 are disposed on an external surface of hollow slats 310, the delivery needles 308 in fluidic communication with the lumen of the hollow slats 310. The delivery needles extend radially outward from the external surface of the hollow slats 310.

In one embodiment of the invention, expandable member 304 is self-expanding, and the hollow slats 310 comprise a self-expanding material such as nitinol. In this embodiment, when the expandable member 304 emerges either from the retractable sheath 312 or from the distal end of the lumen of the catheter 302, expandable member 304 automatically expands to its expanded configuration shown in FIG. 3C. In an alternative embodiment, the hollow slats 310 are mounted over an expandable balloon that may be expanded by the operator. In either embodiment, when expandable member 304 assumes an expanded configuration, the external surface of the slats 310 press against the vessel wall, and the hollow needles 308 pierce the tissue of the wall.

A therapeutic agent is delivered to the treatment site by attaching a syringe to the fitting 306, and injecting the therapeutic agent through the delivery lumen, through the hollow slats 310, and out through the hollow needles 308. In one embodiment of the invention, the therapeutic agent will be injected into the tissue of the vascular wall to a depth defined by the length of the hollow needles 308.

Figure 4A:
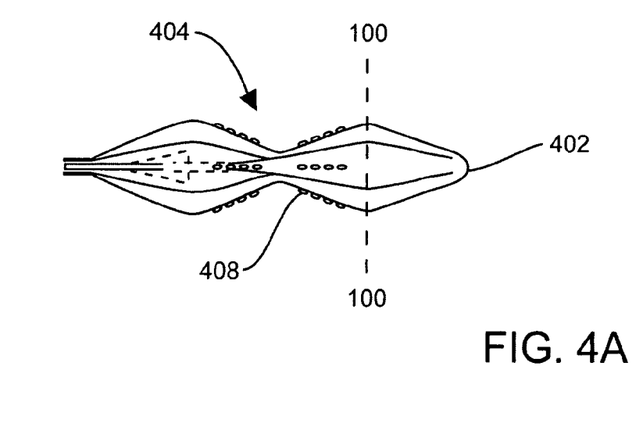
FIG. 4A is a schematic representation of an alternative expandable member in a contracted configuration, in accordance with one aspect of the present invention.

FIG. 4A is a schematic representation of an alternative embodiment 400 of an expandable member 404 in accordance with the invention. Expandable member 404 comprises hollow slats, and may be mounted adjacent to the distal tip of a catheter such as catheter 302 shown in FIG. 3A. In its closed configuration, expandable member 404 has a dumbbell shape as shown in FIG. 4A, in which the drug delivery needles 408 are sequestered in a depression formed by the two ends of expandable member 404. In this configuration, the drug delivery needles are protected from bending or being damaged. In one embodiment of the invention, expandable member 404 is at least partially disposed within a retractable sheath that extends distally to 100-100 in FIG. 4A. In another embodiment of the invention, expandable member 404 is positioned within the distal portion of the lumen of the catheter to 100-100 in FIG. 4A. In either of these embodiments, the closed expandable member 404 presents a smooth exterior with a cone shaped tip 402 during transit to the treatment site.

Figure 4B:
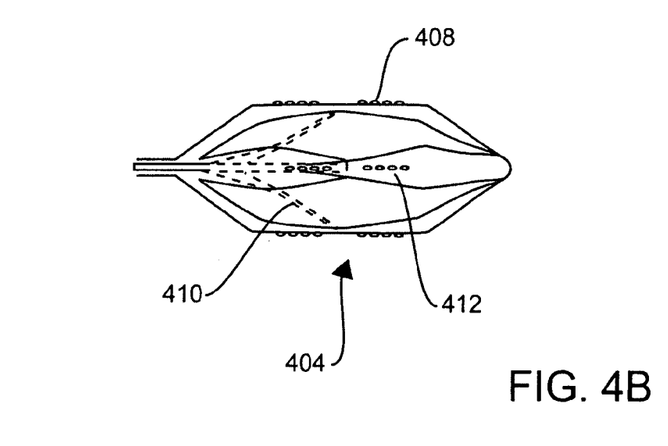
FIG. 4B is a schematic representation of the alternative expandable member of FIG. 4A in an expanded configuration, in accordance with the present invention.

In one embodiment of the invention, expandable member 404 is self-expanding, and comprises a shape memory material such as, for example, nitinol. In an alternative embodiment, a spring at the proximal end of the central portion of expandable member 404 causes support members 410 to open laterally. In either case, expandable member 404 transitions to an expanded configuration as shown in FIG. 4B. In its expanded configuration, the outer surface of expandable member 404 presses against the vessel wall at the treatment site, and the drug delivery needles 408 puncture the tissue and deliver a therapeutic agent into the tissue at a defined depth, determined by the length of the needles 408. Because of its open construction, expandable member 404 disrupts blood flow minimally while in an expanded configuration. Consequently, the time required for drug delivery need not be limited by a need to restore blood flow to the surrounding tissue.

In one embodiment of the invention, additional drug delivery ports are located on the central portion 412 of expandable member 402. In this embodiment, the drug delivery needles 408 and the drug delivery ports 412 are connected to a valve at the proximal end of expandable member 404. The valve may be used to direct the flow of therapeutic agent to either the needles 408 or the ports 412. Consequently, different drugs may be delivered sequentially to the vessel wall and to the interior of the vessel. The valve is connected to a valve control at the proximal end of the catheter.

Figure 5:
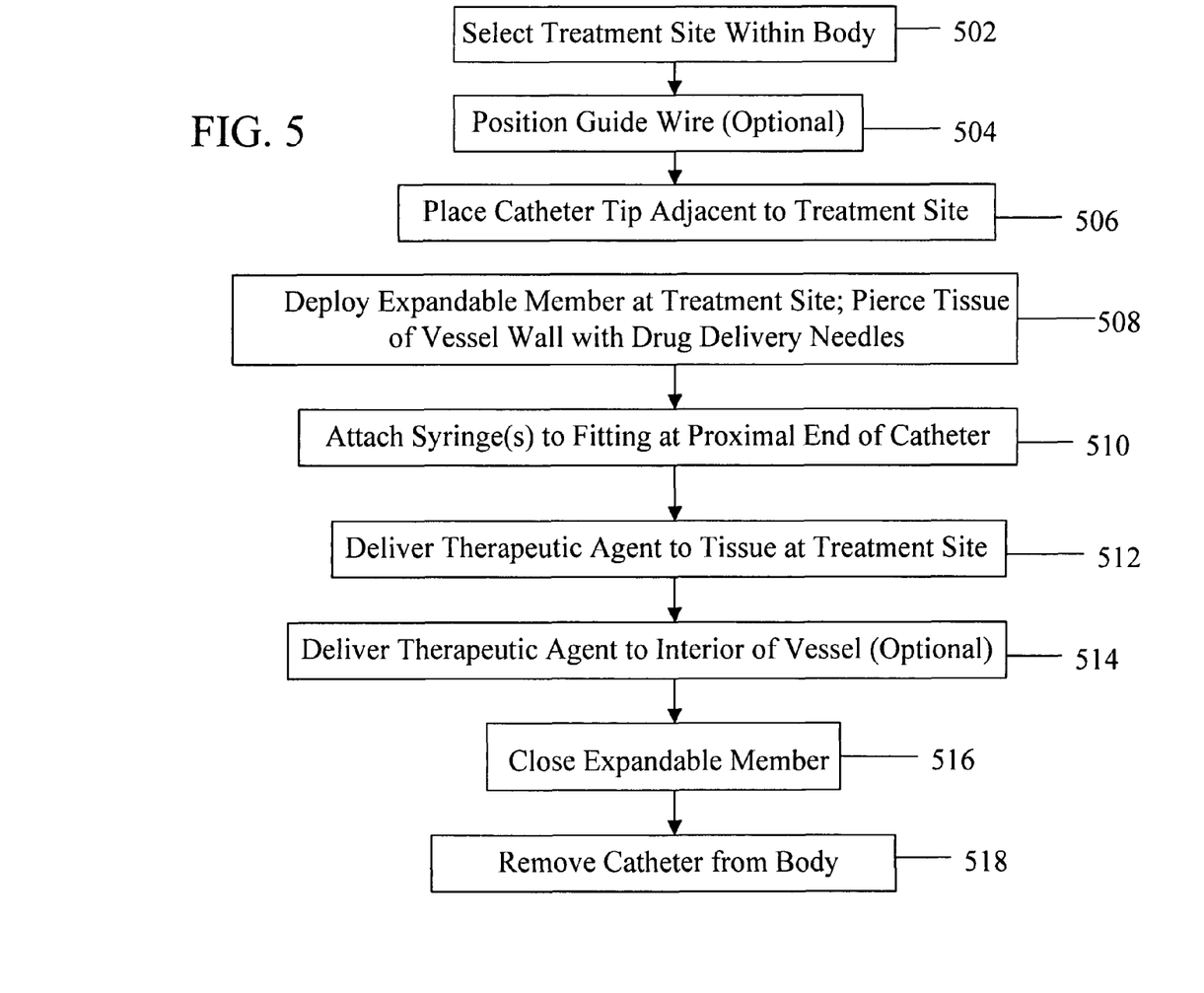
FIG. 5 is a flow diagram of a method for delivering a therapeutic agent to a target site using the delivery devices of FIGS. 3A-4B, in accordance with the present invention.

Another embodiment of the invention includes a method 500 for treating a vascular condition, as illustrated in a flow diagram in FIG. 5. Method 500 begins at block 502 wherein a target site is selected. Next, as indicated in block 504, a guide wire may be inserted into the femoral artery or at another desired site, and advanced to the target site. The catheter is then slipped over the guide wire and threaded through the vascular system until the distal tip of the catheter is placed adjacent to the target site, as indicated in block 506. Next, as indicated in block 508, the expandable member at the distal tip of the catheter is deployed at the treatment site, either by retracting a sheath or by advancing the expandable member out of an inner lumen of the catheter. The expandable member is expanded until the outer surface of the expandable member contacts the vessel wall and the drug delivery needles pierce the tissue of the vessel wall.

One or more syringes containing the therapeutic agent(s) to be delivered to the treatment site are attached to a fitting at the proximal end of the catheter, as indicated in block 510. The therapeutic agent(s) is then injected from the syringe, through the delivery lumen of the catheter, through the hollow slats of the expandable member out through the drug delivery needles, into the tissue of the vessel wall at a defined depth determined by the length of the needles as indicated in block 512. If desired, a therapeutic agent may be then be administered to the interior of the vessel through drug delivery ports on the central portion of the expandable member.

As indicated in block 514, the expandable member is returned to a closed configuration, either by advancing the retractable sheath over the expandable member, or by retracting the expandable member into the lumen of the catheter. Finally, as indicated in block 516, the catheter may be removed from the body.

While the invention has been described with reference to particular embodiments, it will be understood by one skilled in the art that variations and modifications may be made in form and detail without departing from the spirit and scope of the invention.

What is claimed is:

1. A system for treating a vascular condition, comprising:
   a catheter having a proximal end and a distal tip, the catheter including only a single drug delivery lumen formed therein longitudinally from the proximal end to the distal tip;
   at least one expandable jaw device comprising a plurality of jaw segments, wherein a proximal end of each of the plurality of the jaw segments is attached adjacent a distal end of the catheter via a hinge and wherein a distal end of each of the plurality of the jaw segments is unattached to the catheter in both a closed delivery configuration and an open configuration for drug delivery, each of the plurality of the jaw segments including a plurality of drug delivery ports in communication with the drug delivery lumen, wherein each of the plurality of the jaw segments is hollow so a therapeutic agent is deliverable from the drug delivery lumen, through the plurality of the jaw segments, and to the plurality of drug delivery ports.

2. The system of claim 1 further comprising a push rod jaw control device connected to the jaw device and operable from a proximal end of the catheter.

3. The system of claim 1 wherein the jaw device is self expanding.

4. The system of claim 1 wherein the expandable jaw device comprises nitinol.

5. The system of claim 1 wherein contact surfaces of the plurality of jaw segments contact a substantial portion of a target region of a vessel wall.

6. The system of claim 1 further comprising a syringe fitting attached on the proximal end of the catheter.

7. The system of claim 6 wherein the syringe fitting comprises one of a pressure fitting or a luer fitting.

8. The system of claim 1 wherein the drug delivery ports comprise hollow needles extending from an external surface of the jaws wherein the needles are configured to penetrate the vascular tissue and infuse the therapeutic agent to a defined depth within the vascular tissue when the jaws are opened at a target site.

9. The system of claim 1 wherein the expandable jaws are surrounded by a retractable sheath.

10. The system of claim 1 wherein the therapeutic agent is selected from the group consisting of an antirestenotic drug, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, an organic drug, a pharmaceutical compound, a recombinant DNA product, a recombinant RNA product, a collagen derivative, a protein, a protein analog, a saccharide, a saccharide derivative, a bioactive agent, a pharmaceutical drug, a therapeutic substance, or combinations thereof.

* * * * *